US008884096B2

(12) United States Patent
Lifke et al.

(10) Patent No.: US 8,884,096 B2
(45) Date of Patent: Nov. 11, 2014

(54) METHOD FOR THE PRODUCTION OF ANTIBODIES

(71) Applicant: Hoffmann-La Roche Inc., Nutley, NJ (US)

(72) Inventors: Alexander Lifke, Penzberg (DE); Valeria Lifke, Penzberg (DE); Bernd Mueller-Beckmann, Gruenstadt (DE); Tobias Schnitzer, Iffeldorf (DE)

(73) Assignees: Alexander Lifke, Penzberg (DE); Valeria Lifke, Penzberg (DE); Bernd Mueller-Beckmann, Gruenstadt (DE)

( * ) Notice: Subject to any disclaimer, the term of this patent is extended or adjusted under 35 U.S.C. 154(b) by 0 days.

(21) Appl. No.: 13/798,280

(22) Filed: Mar. 13, 2013

(65) Prior Publication Data

US 2013/0189270 A1 Jul. 25, 2013

Related U.S. Application Data

(63) Continuation of application No. 13/443,917, filed on Apr. 11, 2012, now abandoned, which is a continuation of application No. 12/603,642, filed on Oct. 22, 2009, now abandoned, which is a continuation of application No. 11/801,614, filed on May 8, 2007, now abandoned.

(30) Foreign Application Priority Data

May 11, 2006 (EP) ..................................... 06009703

(51) Int. Cl.
*C12P 21/00* (2006.01)
*A61K 35/26* (2006.01)
*A61K 35/28* (2006.01)
*A61K 35/54* (2006.01)
*A61K 35/407* (2006.01)
*A01N 63/00* (2006.01)
*A01N 65/00* (2009.01)
*C12N 5/0781* (2010.01)
*C07K 16/00* (2006.01)
*C07K 16/28* (2006.01)
*C07K 16/32* (2006.01)

(52) U.S. Cl.
CPC ............... *C12P 21/00* (2013.01); *C12N 5/0635* (2013.01); *C07K 16/00* (2013.01); *C07K 16/2866* (2013.01); *C07K 16/32* (2013.01)
USPC ............... 800/6; 424/577; 424/582; 424/553; 424/93.7

(58) Field of Classification Search
CPC ........... A01K 67/0271; A01K 2217/00; A01K 2267/01; C07K 14/70503
USPC ........ 800/14, 6; 435/325; 424/93.1, 577, 582, 424/553, 93.7
See application file for complete search history.

(56) References Cited

U.S. PATENT DOCUMENTS

| 5,434,341 A | 7/1995 | Outzen |
| 5,658,570 A | 8/1997 | Newman et al. |
| 2004/0258694 A1 | 12/2004 | Abrignani et al. |
| 2005/0155094 A1 | 7/2005 | Yasue et al. |

FOREIGN PATENT DOCUMENTS

| CN | 1198648 C | 4/2005 |
| EP | 0322240 | 3/1995 |
| EP | 1645183 | 4/2006 |
| WO | 96/40252 | 12/1996 |
| WO | WO 96/40252 | 12/1996 |
| WO | WO 97/41224 A1 * | 11/1997 |
| WO | 03/068915 | 8/2003 |

OTHER PUBLICATIONS

Wols et al., Plasma Cells, Encyclopedia of Life Sciences, p. 1, 2005, who states, "Plasma cells are terminally differentiated B-lymphocytes."*
Sanhadji, K. et al., Thymus 15(1):57-64 ( 1990).
Lacuad, G. et al., Immunity 9(6):827-838 ( 1998).
Shinkai, Y. et al., Cell 68:855-867 ( 1992).
(AACR Poster/Abstract2007).
http://bioweb.uwlax.edu/GenWeb/Molecular/Seq_Anal/Seq_Comparison/seq_comparison.html publically available 2003. (Homology accessed on-line at Nov. 3, 2011).
Jankowski et al., Human Immunology 52:155-161 ( 1997).
Cole et al., Monoclonal Antibodies and Cancer Therapy:77-96 ( 1985).
Matsumura, T. et al., Exp.. Hematology 31:789-797 ( 2003).
ABBAS Cellular and Molecular ImmunologyElsevierSaunders, vol. 5th:11 ( 2005).
Smith Encyclopedia of Life Sciences:1-10 ( 2001).
Gotherstrom et al., Bone Marrow Transplantation 32:265-272 ( 2003).
Horton, R. M. et al., Biotechniques 19:690-691 ( 1995).
Zuniga-Pfluecker, J.C. et al., J.Exp. Med. 180:1517-1521 ( 1994).
McBride, Methods in Molecular Medicine Vaccine Protocols 4:231-233 ( 2003).
Marks, J.D. et al., Journal of Molecular Biology 222:581-597 ( 1991).
Jakobovits, A. et al., Proc. Natl. Acad. Sci. USA 90:2551-2555 ( 1993).
Disanto, J.P. et al., Proc. National Academy Science 92:377-381 ( 1995).
Traggai, E. et al., Science 304:104-107 ( 2004).
Dempsey, Biotechnol. Progress 19:175-178 ( 2003).

(Continued)

*Primary Examiner* — Thaian N Ton
(74) *Attorney, Agent, or Firm* — Paul D. Strain, Esq.; Strain & Strain PLLC

(57) ABSTRACT

The current invention is related to a method for the production of a human monoclonal antibody from a immunodeficient non-human animal, said method comprising contacting a new borne immunodeficient non-human animal with a human fetal liver stem cell (FL cell) to generate an immune transplanted non-human animal (reconstituted animal), subsequently contacting said reconstituted animal with a antigen, collecting from said reconstituted animal a human cell producing human antibody against said antigen, and isolating said antibody from said antibody producing cell.

11 Claims, 10 Drawing Sheets

(56) References Cited

OTHER PUBLICATIONS

Jakobovits, A. et al., Nature 362:255-258 (1993).
Peault,B. et al., J.Exp. Med. 174:1283-1286 (1991).
Boerner, P. et al., Journal of Immunology 147:86-95 (1991).
Malynn, B.A. et al., Int. Immunology 7:1637-1647 (1995).
Hoogenboom, H.R. et al., Journal of Molecular Biology 227:381-388 (1992).
http://www.criver.com/sitecollectiondocuments/rm_rm_d_immunodeficient_models.pdf, pp. 1-4 (Charles River=Accessed on line Feb. 7, 2011).
Kollet et al., Blood 97:3283-3291 (2001).
Covens et al., "Characterization of proposed human B-1 cells reveals pre-plasmablast phenotype", Blood, vol. 121, No. 26 (2013), pp. 5176-5183.
Kuroiwa et al., "Cloned transchromosomic calves producing human immunoglobin", Nature Biotechnology, vol. 20 (2002), pp. 889-894.
Meyerrose et al., "Immune-deficient mouse models for analysis of human stem cells", BioTechniques, vol. 35 (2003), pp. 1262-1272.
Watanabe et al., "A Novel Method for the Production of Transgenic Cloned Pigs: Electroporation-Mediated Gene Transfer to Non-Cultured Cells and Subsequent Selection with Puromycin", Biology of Reproduction, vol. 72 (2005), pp. 309-315.
Shapiro-Shelef et al., "Regulation of Plasma-Cell Development", Nature Publishing Group, vol. 5 (2005), pp. 230-242.
Wols et al., "Plasma Cells", Encyclopedia of Life Sciences (2005), 9 pgs.
Chinese Office Action and English translation thereof, Appl. No. 200780008799.7, May 6, 2014.
Peichev et al., "Expression of VEGFR-2 and AC133 by circulating human CD34+ cells identifies a population of functional endothelial precursors", Blood, vol. 95 (2000), pp. 952-958.
Samhadji et al., "Fetal liver cell transplantation in scid mice", Thymus, vol. 15 (1990), pp. 57-64.
Chinese Office Action and English translation thereof, Appl. No. 2007800087997, Jul. 22, 2014, 35 pgs.
K. Sanhadji et al., "Fetal liver cell transplantation in various murine models", Transplantation and Clinical Immunology Unit, Bone Marrow Transplant (1992), pp. 77-82.

\* cited by examiner

METHOD FOR THE PRODUCTION OF ANTIBODIES

PRIORITY TO RELATED APPLICATION(S)

This application is a continuation of application Ser. No. 13/443,917, filed Apr. 11, 2012, now pending; which is a continuation of application Ser. No. 12/603,642 filed Oct. 22, 2009, now pending which is a continuation of application Ser. No. 11/801,614 filed May 8, 2007, now pending which claims the benefit of European Patent Application No. 06009703.7, filed May 11, 2006, which is hereby incorporated by reference in its entirety.

FIELD OF THE INVENTION

The present invention generally relates to methods for the production of antibodies, compositions of antibody producing cells, methods for their production and uses thereof.

BACKGROUND OF THE INVENTION

Monoclonal antibodies (MAB) have long been considered as magic bullets in immunotherapy of cancer, infection or autoimmune disease etc. However, the first generation of murine antibodies which were used in humans was rather unsuccessful due to human anti-mouse immune responses.

Human antibodies have been mostly either derived from transgenic mice harboring a restricted set of human Ig genes or selected from large artificial antibody libraries using phage display, yeast display or similar recombinant technologies. These strategies have been designed to eliminate any immune reaction against the monoclonal antibody in the human background. Human antibodies can be produced in transgenic animals (e.g. mice) that are capable, upon immunization, of producing human antibodies in the absence of endogenous immunoglobulin production. Transfer of the human germ line immunoglobulin gene array in such germ line transgenic mice result in the production of human antibodies upon antigen challenge (see, e.g., van Dijk, M. A. and van de Winkel, J. G., Curr. Opin. Chem. Biol. 5 (2001) 368-374; Jakobovits, A., et al., Proc. Natl. Acad. Sci. USA 90 (1993) 2551-2555; Jakobovits, A., et al., Nature 362 (1993) 255-258; Bruggemann, M., et al., Year Immunol. 7 (1993) 33-40). Human antibodies can also be produced in phage display libraries (Hoogenboom, H. R. and Winter, G., J. Mol. Biol. 227 (1992) 381-388; Marks, J. D., et al., J. Mol. Biol. 222 (1991) 581-597). The techniques of Cole et al. and Boerner et al. are also available for the preparation of human monoclonal antibodies (Cole et al., Monoclonal Antibodies and Cancer Therapy, Alan R. Liss, p. 77 (1985); and Boerner, P., et al., J. Immunol. 147 (1991) 86-95). However such transgenic mice are only capable to provide antibodies wih a restricted set of human Ig genes—those which result from the transfected immunoglobulin gene array.

The methodologies based on mice transgenic for human immunoglobulin genes have allowed the generation of antibodies derived from human germ line sequence, which has reportedly reduced the immunogenicity of the resulting antibody drugs compared to murine or mouse-human chimeric antibodies. However, transgenic mouse-derived human antibodies are limited in their diversity, affinities and specificities compared to natural human immune repertoires.

Similarly, a major drawback of phage or yeast display-based combinatorial library approaches is the random pairing of the antibody heavy and light chains. The dissociation of the original antibody heavy and light chain pairing, non-cognate pairing, necessitate the screening of a large number of clones in order to identify heavy and light chain pairs of high affinity. In addition, such non-cognate pairs may display unwanted cross-reactivity to human self-antigens. Finally, the genetic diversity of target-specific antibodies identified by selection and screening of combinatorial libraries is commonly limited due to inherent selection biases.

Traggai, E. et al., Science 304 (2004) 104-107 describe a method for the development of a human immune system in human cord blood cell-transplanted Rag 2−/−γc−/−mice, which can be used as a preclinical model to evaluate responses to vaccines or live infectious pathogens and to pharmacological compounds that target the human immune system. It was shown that reconstituted and subsequently pathogen vaccinated mice can produce tetanus toxoid specific antibody responses at low levels. However, the method of Traggai et al utilized the non-human pseudomonas exotoxin antigen. There is a need for a methodology for production of a human monoclonal antibody in a reconstituted animal wherein, inter alia, the reconstituted animal can produce human antibodies against a human antigen in a high amount.

SUMMARY OF THE INVENTION

The invention comprises a method for the production of a human monoclonal antibody from a immunodeficient non-human animal, said method comprising contacting a new borne immunodeficient non-human animal with a human fetal liver stem cell (FL cell) to generate an immune transplanted non-human animal (reconstituted animal), subsequently contacting said reconstituted animal with an antigen, collecting from said reconstituted animal a human cell producing human antibody against said antigen, and isolating said antibody from said antibody producing cell.

The invention preferably comprises a method according to the invention, characterized in establishing of said antibody producing cell an immortal antibody producing cell preferably by a transformation method or cell fusion method. Preferably said immortal cell is capable of being viable for at least 50 passages.

Preferably said non-human animal is a rodent and more preferably a mouse, rat or rabbit. It is further preferred that the mouse is a Rag2−/−γc−/−, nude Rag 2−/−, NOD (NOD means according to the invention preferably NOD.Cg-Rag1$^{tm1Mom}$Prf1$^{tm1Sdz}$/SzJ) or SCID beige mouse and the rat is a nude rat.

The invention comprises a method according to the invention, characterized in that said FL cell is a human hematopoietic fetal liver stem cell (HFL cell), preferably CD133+, CD 117+, CD 31+ and/or CD34+.

The invention additionally comprises a method for the production of a plurality of human B cells producing a complete plurality of human antibodies against a antigen said method is characterized by contacting a new borne immune deficient non-human animal with a FL cell to generate a immuno reconstituted animal, subsequently contacting said reconstituted animal with a antigen, collecting said human B cells, producing said complete plurality of antibodies.

A:
Numerator Histogram
File: Probe.002
X Parameter: Anti-hu-CD45-FITC
Denominator Histogram
File: Probe.001
X Parameter: Anti-hu-CD45-FITC

| Marker | Events | % Gated |
|---|---|---|
| All | 18110 | 108.79 |
| M1 | 16705 | 100.35 |
| M2 | 860 | 5.17 |

B:
Numerator Histogram
File: Probe.004
X Parameter: Anti-hu-CD45-FITC
Denominator Histogram
File: Probe.003
X Parameter: Anti-hu-CD45-FITC

| Marker | Events | % Gated |
|---|---|---|
| All | 14622 | 231.91 |
| M1 | 11833 | 187.68 |
| M2 | 2136 | 33.88 |

C:
Numerator Histogram
File: Probe.006
X Parameter: Anti-hu-CD45-FITC
Denominator Histogram
File: Probe.005
X Parameter: Anti-hu-CD45-FITC

| Marker | Events | % Gated |
|---|---|---|
| All | 4181 | 95.59 |
| M1 | 2992 | 68.40 |
| M2 | 844 | 19.30 |

Figure 2:
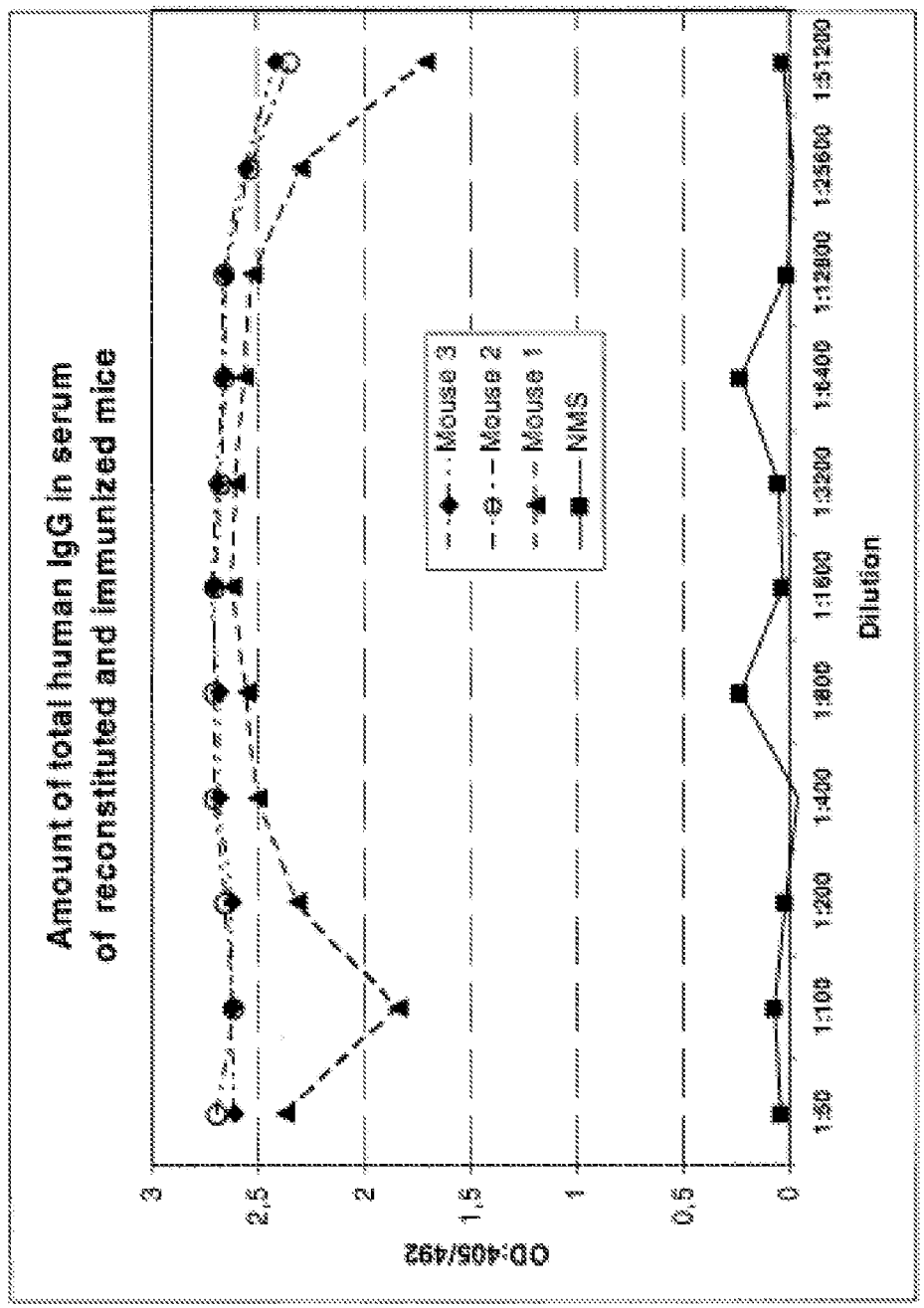
Figure 3A:
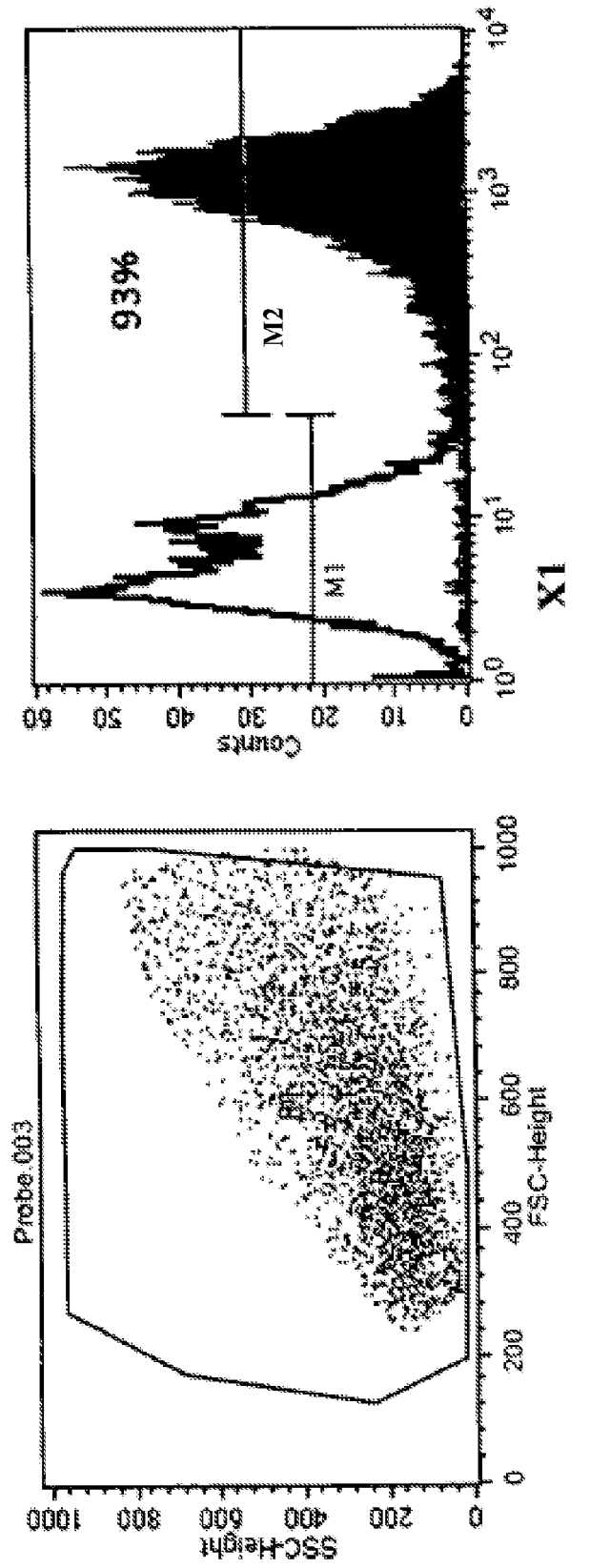
Figure 3B:
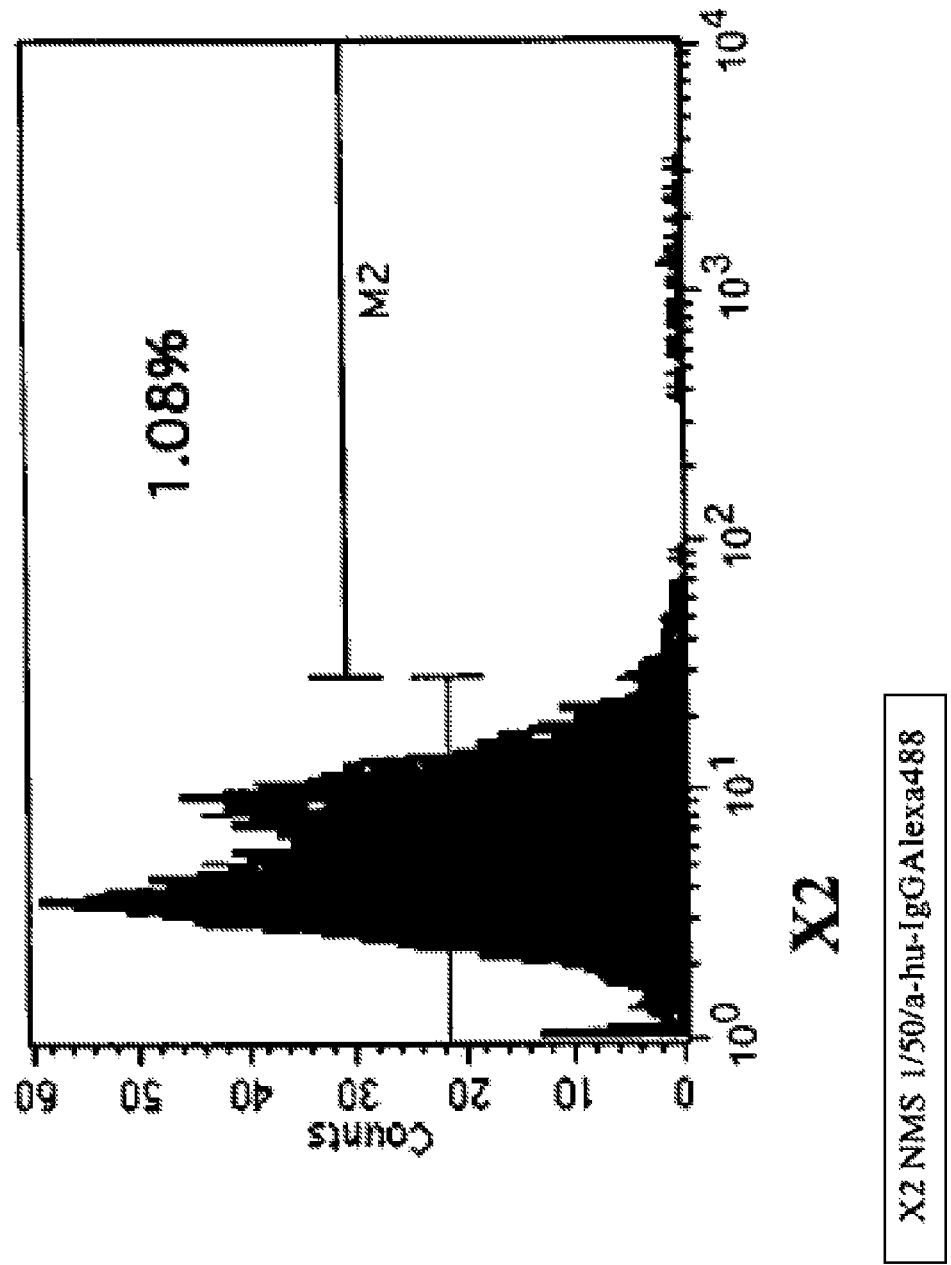
Figure 3C:
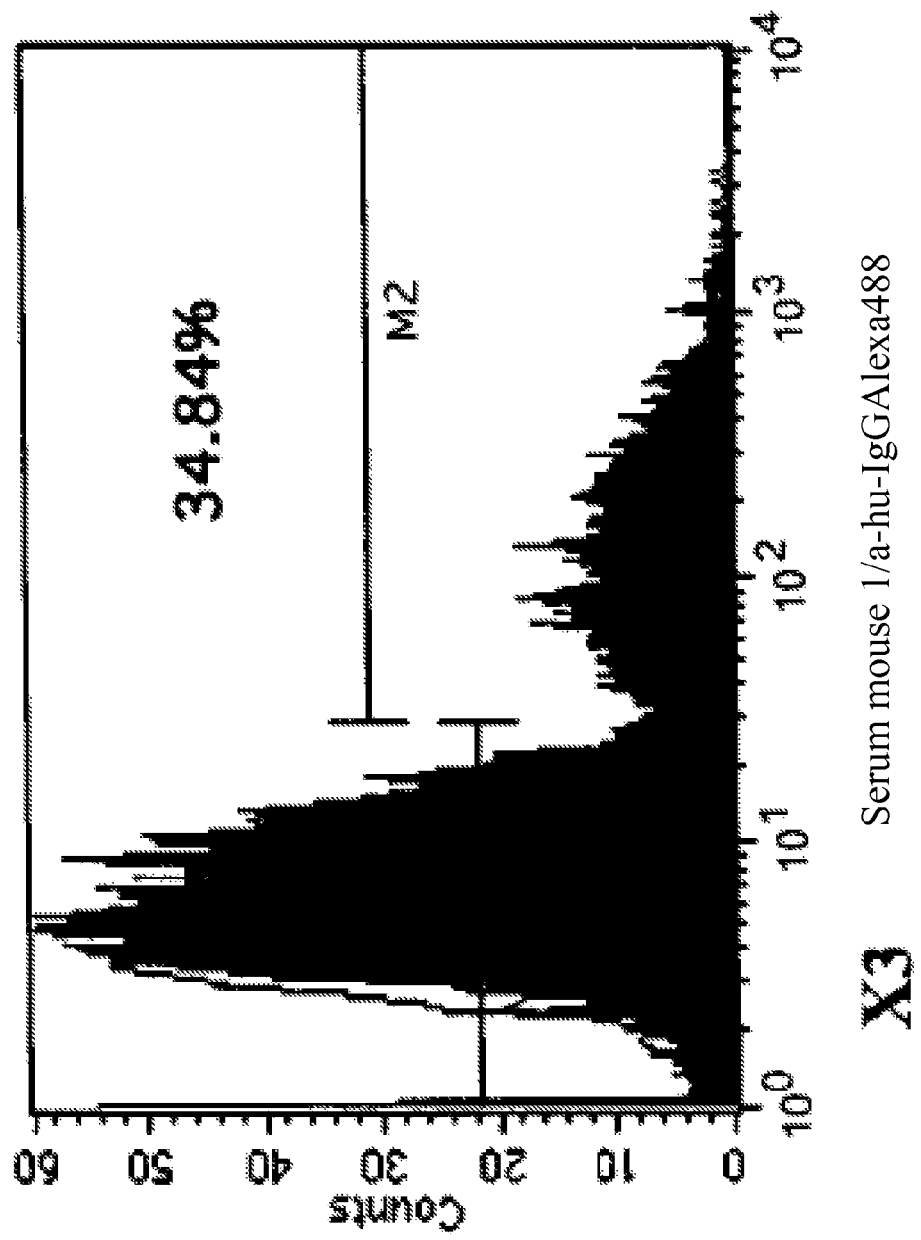
Figure 3D:
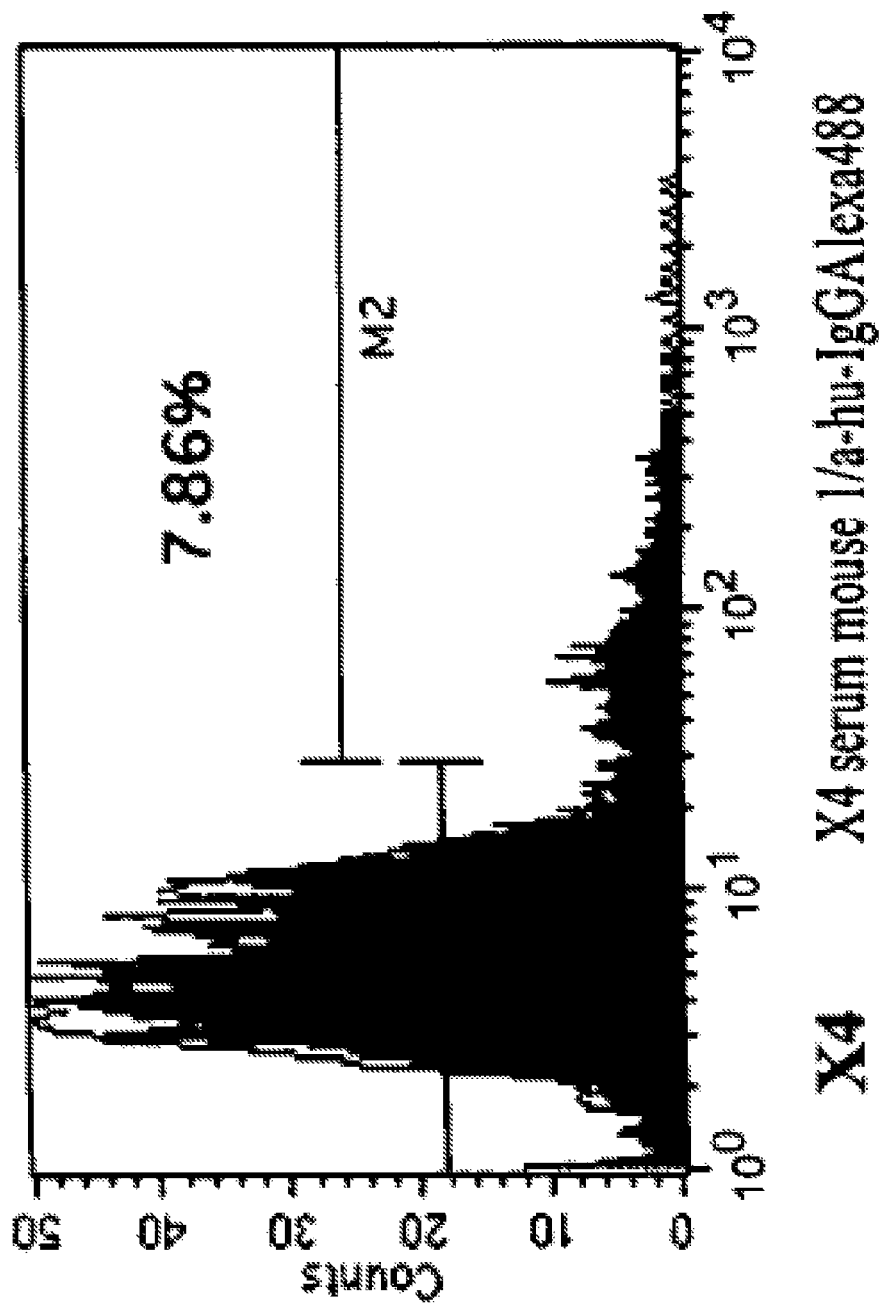

FIG. 2 Examination of the production ability of human antibodies in the reconstituted mice.

FIG. 3 Flowcytometric analysis of human antigen specific antibodies in peripheral blood of reconstituted mice on 7th week after immunization Shown is ratio (%) of antigen positive cells stained with different serum dilution (1/20 (C) and 1/150 (D)) of one representative reconstituted and immunized mouse compared to normal serum of control mouse (NMS) as negative control (2nd histogram (B)) or to purified antigen specific antibodies as a positive control (upper histogram (A)). Statistics represent number and percentage of events in designated sections (M2 and M1 markers show cells stained positive or negative for antigen respectively) compared to total number of events within the gate. Shown are mean fluorescent intensities.

A: Positive Control
Numerator Histogram
Total Events: 6764
Denominator Histogram
Total Events: 7072

| Marker | % Gated | % Total |
|---|---|---|
| All | 95.54 | 95.05 |
| M1 | 2.02 | 2.01 |
| M2 | 93.55 | 93.07 |

B: Negative Control NMS
Numerator Histogram
Total Events: 7093
Denominator Histogram
Total Events: 7072

| Marker | % Gated | % Total |
|---|---|---|
| All | 100.38 | 99.87 |
| M1 | 99.33 | 98.83 |
| M2 | 1.08 | 1.07 |

C: Serum Mouse 1 (1/20) vs. NMS
Numerator Histogram
Total Events: 15544
Denominator Histogram
Total Events: 7093

| Marker | % Gated | % Total |
|---|---|---|
| All | 160.13 | 159.45 |
| M1 | 125.33 | 124.80 |
| M2 | 34.84 | 34.70 |

D: Serum Mouse 1 (1/150) vs. NMS
Numerator Histogram
Total Events: 7102
Denominator Histogram
Total Events: 7093

| Marker | % Gated | % Total |
|---|---|---|
| All | 100.03 | 99.61 |
| M1 | 92.18 | 91.79 |
| M2 | 7.86 | 7.82 |

Figure 4:
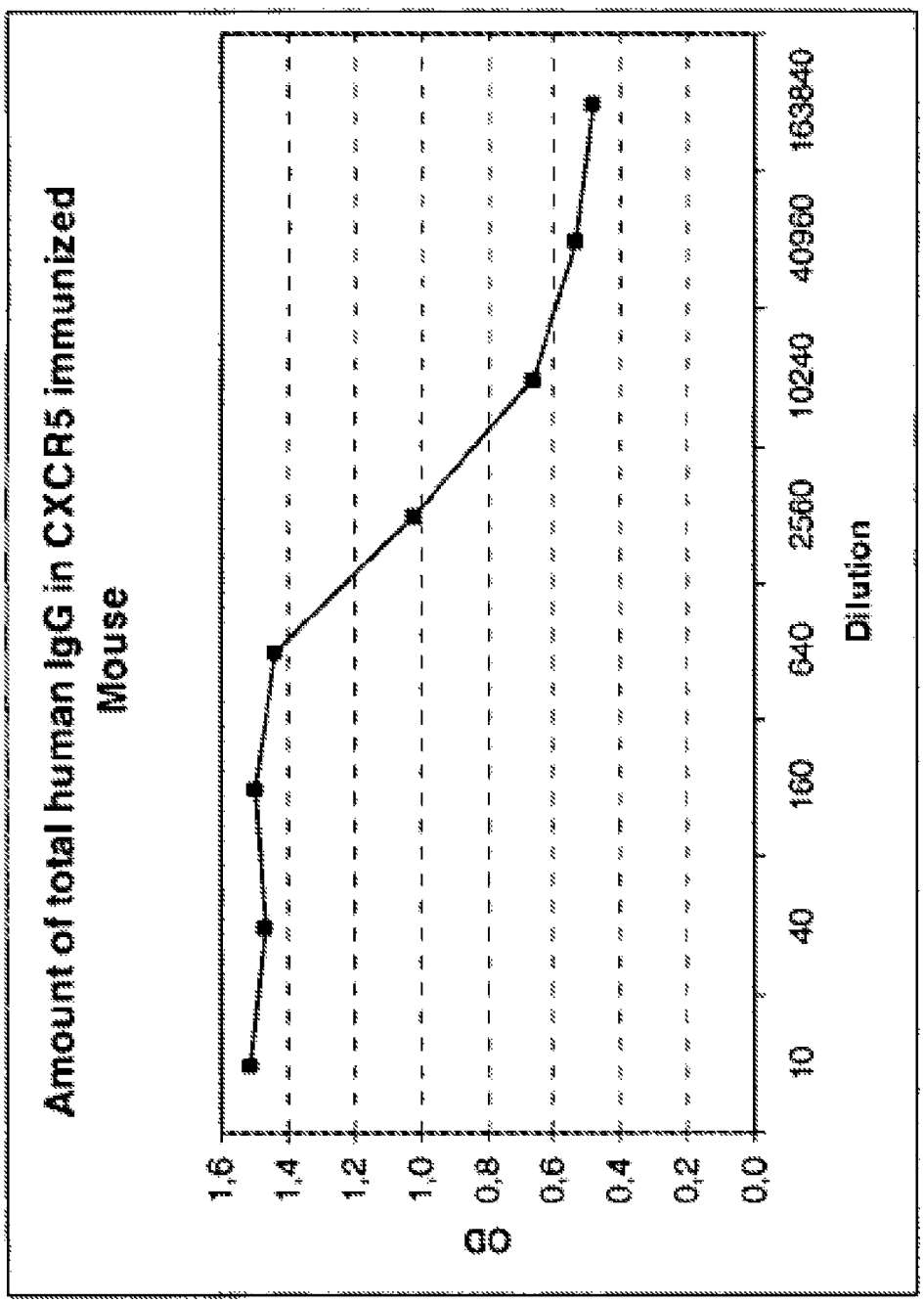

FIG. 4 Examination of the production ability of human CXCR5 antibodies in the reconstituted mice.

Figure 5:
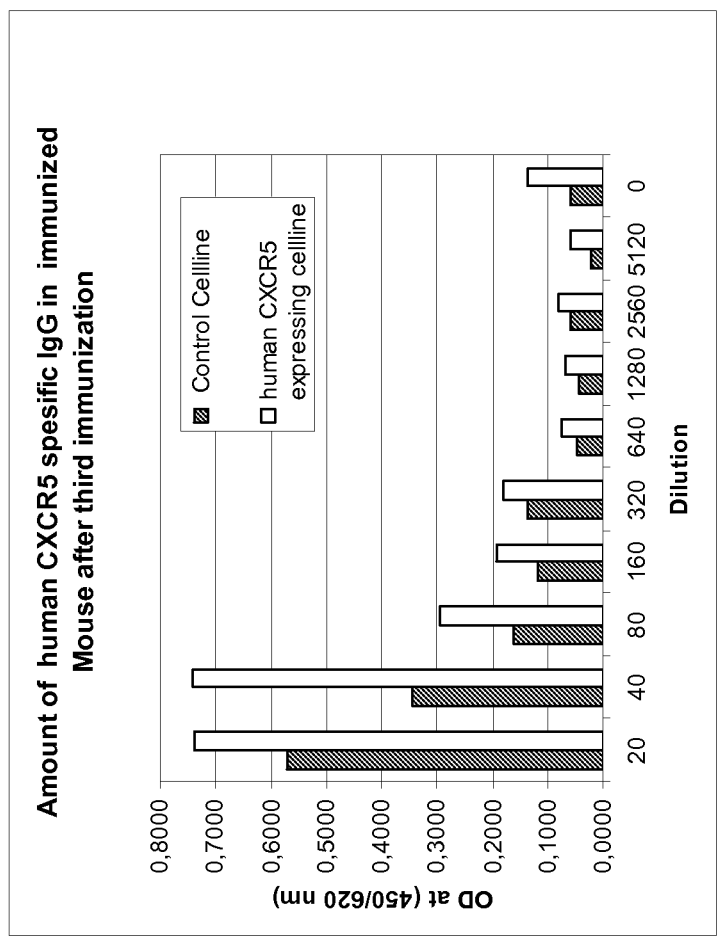

FIG. 5 Examination of the production ability of human CXCR5 specific antibodies in the reconstituted mice after third immunization.

DESCRIPTION OF THE INVENTION

A. Definitions

The term "complete plurality of human antibodies or human immunoglobulin genes" refers to antibodies or immunoglobulin genes comprising or encoding kappa chains from at least 20, preferably 31 to 33 kappa genes at 2p11 on chromosome 2 (76 genes, of which 31 to 35 are functional), lambda chains from at least 20, preferably 29 to 33 lambda genes at the 22q11 position on chromosome 22 and a J gene;

(there are 4 to 5 functional lambda chain genes, each of which is preceded by a lambda J gene), and heavy chains from at least 5, preferably 9 heavy genes at 14q32 on chromosome 14 (11 heavy chain genes, 9 of which are functional and correspond respectively to 9 heavy chain isotypes μ, δ, γ1, γ2, γ3, γ4, α1, α2 and ε).

For example, the antigen can be a substance derived from human, like a human protein, a hormone, a tumor-associated glycolipid (e.g. U.S. Pat. No. 5,091,178) or another substance involved in natural occuring human metabolism. The antigen can also be a non-human derived substance which is tolerated by a healthy human being so that such human being do not develop antibodies in a detectable manner against such antigen.

The term "human protein" (which includes polypeptides) refers to an arbitrary protein of a human being which is either naturally tolerated or attacked in autoimmune diseases. The term human protein includes according to the knowledge of a person skilled in the art also fragments of said protein which are capable of inducing antibodies specific for such a human protein in the non human animal suitable according to the invention. Such fragments can be included for example in a larger protein, e.g. it is well known that antibodies against human proteins can be induced by immunization with a homogue protein from another species like mouse. The human protein is preferably a tolerated human protein.

The term "tolerated human" protein refers to a protein of a human being which is naturally tolerated and not attacked in autoimmune diseases like Goodpasture's Syndrome, Insulin dependent diabetes mellitus (IDDM), Immune hemolytic anemia, Immune thrombocytopenic purpura, Myasthenia gravis (MG), Multiple sclerosis (MS), Rheumatoid arthritis, Systemic lupus erythematosus (SLE) or Thyrotoxicosis (Graves' disease).

For example, the human protein may be a transmembrane molecule (e.g. receptor) or ligand such as a growth factor. Exemplary antigens include molecules such as renin; a growth hormone, growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor VIII, factor IX, tissue factor (TF), and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin such as human serum albumin; Muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; vascular endothelial growth factor (VEGF); receptors for hormones or growth factors; protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-b; platelet-derived growth factor (PDGF); fibroblast growth factor such as aFGF and bFGF; epidermal growth factor (EGF); transforming growth factor (TGF) such as TGF-alpha and TGF-beta, including TGF-b1, TGF-b2, TGF-b3, TGF-b4, or TGF-b5; a tumor necrosis factor (TNF) such as TNF-alpha or TNF-beta; insulin-like growth factor-I and -II; insulin-like growth factor binding proteins; CD proteins such as CD3, CD4, CD8, CD 19, CD20, CD22 and CD40; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1, IL-2, IL-3, IL-4, IL-5, IL-6, IL-7, IL-8, IL-9 and IL-10; superoxide dismutase; T-cell receptors; surface membrane proteins; decay accelerating factor; viral antigen such as, for example, a portion of the AIDS envelope; transport proteins; homing receptors; addressins; regulatory proteins; integrins such as CD11a, CD11b, CD11c, CD18, an ICAM, VLA-4 and VCAM; a tumor associated antigen such as HER2, HER3 or HER4 receptor; and fragments of any of the above-listed proteins. Further human proteins are members of the ErbB receptor family such as the EGF receptor, HER2, HER3 or HER4 receptor; a member of the tumor necrosis receptor superfamily, including DR5; prostate stem cell antigen (PSCA); cell adhesion molecules such as LFA-1, Mac1, p150.95, VLA-4, ICAM-1, VCAM, alpha4/beta7 integrin, and alphav/beta3 integrin including either alpha or beta subunits thereof (e.g. anti-CD11a, anti-CD18 or anti-CD11b antibodies); tissue factor (TF); alpha interferon (alpha-IFN); an interleukin, such as IL-8; IgE; blood group antigens; flk2/flt3 receptor; obesity (OB) receptor or mp1 receptor.

The term "immortal cell" refers to a hybridoma cell or a cell immortalized by other means, like EDV transformation, telomerase replacement or retroviral immortalizaton.

The term "animal" as used herein refers to a non human animal, preferably a rodent and especially preferred a mouse or rat.

Preferably said non-human animal is a rodent and more preferably a mouse, rat or rabbit. It is further preferred that the mouse is a Rag2–/–γc–/–, nude Rag 2–/–, NOD or SCID beige mouse and the rat is a nude rat.

SCID beige is a double mutant mouse carrying the scid mutation which causes a lack of both T and B lymphocytes due to a defect in V(D)J recombination. It also carries the beige mutation which results in cytotoxic T cell and macrophage defects as well as selective impairment of NK cell functions. SCID beige mice are potentially an improved model for receipt of human hematopoietic cells.

Preferred NOD mice are NOD.Cg-Rag1$^{tm1Mom}$ Prf1$^{tm1Sdz}$/SzJ, NOD.Cg-Prkdc$^{scid}$Il2rg$^{tm1Wjl}$/SzJ, NOD.129S7(B6)-Rag1$^{tm1Mom}$/J, NOD.Cg-Prkdc$^{scid}$ B2m$^{tm1Unc}$/J and NOD.CB17-Prkdc$^{scid}$/SzJ. Every strain lacks mature T and B cells and has no detectable NK cytotoxic activity. The strains support enhanced engraftment with human hematopoietic cells has a relatively longer lifespan and is significantly more resistant to irradiation.

Rag2 is essential for the V(D)J gene rearrangements that generate functional antigen receptors in T and B cells; homozygous Rag2–/– mutants have no mature, functional T and B cells. The common gamma (γc) KO mouse lacks functional receptors for many cytokines including IL-2, IL-4, IL-7, IL-9, and IL-15. As a consequence lymphocyte development is greatly compromised. The mouse lacks Natural Killer (NK) cells and produces only a small number of T and B cells.

The term "human antibody, as used herein, includes antibodies having variable and constant regions (domains) which can be assigned to defined human germ line immunoglobulin sequences because of their high sequence similarity or identity with these germ line sequences. A human antibody encompasses the various forms of antibodies, preferably monoclonal antibodies including but not being limited to whole antibodies, single heavy or light chains, antibody fragments, class-altered antibodies, and genetically engineered antibodies (variant or mutant antibodies) as long as the characteristic properties according to the invention are retained. Especially preferred are recombinant human antibodies. The term "monoclonal antibody" as used herein refers to a preparation of antibody molecules all having substantially the same amino acid sequence.

The term "recombinant human antibody", as used herein, is intended to include all human antibodies that are prepared, expressed, created or isolated by recombinant means, such as antibodies isolated from a host cell such as a NS0, HEK 293 or CHO cell comprising a recombinant expression vector capable of expessing heavy and/or light chain(s) of said antibody and being transfected into such a host cell. Such recombinant human antibodies have variable and constant regions in a rearranged form. The recombinant human antibodies according to the invention have been subjected to in vivo somatic hypermutation. Thus, the amino acid sequences of the VH and VL regions of the recombinant antibodies are sequences that can be assigned to defined human germ line VH and VL sequences, but may not naturally exist within the human antibody germ line repertoire in vivo.

The "variable region" (variable region of a light chain (VL), variable region of a heavy chain (VH)) as used herein denotes each of the pair of light and heavy chains which is involved directly in binding the antibody to an antigen. The domains of variable human light and heavy chains have the same general structure and each domain comprises four framework (FR) regions whose sequences are widely conserved, connected by three "hypervariable regions" (or complementarity determining regions, CDRs). The framework regions adopt $\alpha\beta$(beta)-sheet conformation and the CDRs may form loops connecting the $\beta$-sheet structure. The CDRs in each chain are held in their three-dimensional structure by the framework regions and form together with the CDRs from the other chain the antigen binding site. The antibody heavy and light chain CDR3 regions, preferably the heavy chain CDR3, play a particularly important role in the binding specificity/affinity of the antibodies according to the invention and therefore provide a further object of the invention.

The terms "hypervariable region" or "antigen-binding portion of an antibody" when used herein refer to the amino acid residues of an antibody which are responsible for antigen-binding. The hypervariable region comprises amino acid residues from the "complementarity determining regions" or "CDRs". "Framework" or "FR" regions are those variable domain regions other than the hypervariable region residues as herein defined. Therefore, the light and heavy chains of an antibody comprise from N- to C-terminus the domains FR1, CDR1, FR2, CDR2, FR3, CDR3, and FR4. CDR and FR regions are determined according to the standard definition of Kabat et al., Sequences of Proteins of Immunological Interest, 5th ed., Public Health Service, National Institutes of Health, Bethesda, Md. (1991).

The "constant domains" are not involved directly in binding of an antibody to an antigen, but exhibit various effector functions. Depending on the amino acid sequence of the constant region of their heavy chains, antibodies or immunoglobulins are divided in the classes: IgA, IgD, IgE, IgG and IgM, and several of these may be further divided into subclasses (isotypes), e.g. IgG1, IgG2, IgG3, and IgG4, IgA1 and IgA2. The heavy chain constant regions that correspond to the different classes of immunoglobulins are called $\mu$, $\delta$, $\gamma$, $\alpha$, and $\epsilon$ respectively. All references cited herein are hereby incorporated by reference.

B. Detailed Description of the Invention.

The invention comprises a method for the production of a human monoclonal antibody from a immunodeficient non-human animal, said method comprising contacting a new borne immunodeficient non-human animal with a human fetal liver stem cell (FL cell) to generate an immune transplanted non-human animal (reconstituted animal), subsequently contacting said reconstituted animal with an antigen, collecting from said reconstituted animal a human cell producing human antibody against said antigen, and isolating said antibody from said antibody producing cell.

The invention preferably comprises a method according to the invention, characterized in establishing of said antibody producing cell an immortal antibody producing cell preferably by a transformation method or cell fusion method. Preferably said immortal cell is capable of being viable for at least 50 passages.

Preferably said non-human animal is a rodent and more preferably a mouse, rat or rabbit. It is further preferred that the mouse is a Rag2−/−γc−/−, nude Rag 2−/−, NOD (NOD means according to the invention preferably NOD.Cg-Rag1$^{tm1Mom}$Prf1$^{tm1Sdz}$/SzJ) or SCID beige mouse and the rat is a nude rat.

The invention comprises a method according to the invention, characterized in that said FL cell is a human hematopoietic fetal liver stem cell (HFL cell), preferably CD133+, CD 117+, CD 31+ and/or CD34+.

In a further embodiment the method is preferably characterized in that said FL cell is a combination of a a HFL cell and a human non hematopoeitic fetal liver stem cell.

The invention comprises a method according to the invention, characterized in that said antibody producing cell is a human B-cell.

The invention comprises a method according to the invention, characterized in that said FL cell is for contacting injected i.p., s.c. or intrahepatic into the animal.

The invention comprises a method according to the invention, characterized in that the antigen is a polypeptide, a MHC/peptide complex or DNA.

The invention comprises a method according to the invention, characterized in that the antigen is contacted with the reconstituted animal as antigen, antigen fragment, antigen encoding DNA and/or antigen bearing cell.

The invention comprises a method according to the invention, characterized in that the immune deficient non-human animal is irradiated sublethally before being contacted with the FL cell.

The invention comprises a method according to the invention, characterized in that the mouse is contacted the first time with the antigen 5 to 18 weeks after contacting said mouse with said FL cell.

The invention also comprises a method according to the invention, characterized in that the mouse is contacted up to ten times with the antigen.

The invention also comprises a method according to the invention, characterized in that said collected cell is a human CD19$^+$ or CD22$^+$ cell.

The invention also comprises a method according to the invention, characterized in that said cell is established by hybridoma technology.

The invention also comprises a method according to the invention, characterized in that the fusion partner cell line is a MFP-2, HK-128, K6H6/B5 or Karpas 707 cell line.

The invention additionally comprises a method for the production of a plurality of human B cells producing a complete plurality of human antibodies against a antigen said method is characterized by contacting a new borne immune deficient non-human animal with a FL cell to generate a immuno reconstituted animal, subsequently contacting said reconstituted animal with a antigen, collecting said human B cells, producing said complete plurality of antibodies.

The invention additionally comprises the use of a non-human animal for the production of an antigen producing immortal cell according to the invention. If the immortal cell is a hybridoma cell, one fusion partner for hybridoma generation is a human B cell from said transplanted and reconstituted animal, the other fusion partner is a myeloma cell, e.g. from human, rodent or an other animal. Alternatively immortal transplanted and reconstituted B cells are generated by EBV transformation.

The invention also comprises a plurality of human B cells producing a complete plurality of human antibodies against a human protein.

The invention also comprises a composition of immortal cells providing a complete plurality of human antibodies against a human protein.

The invention additionally comprises the use of a reconstituted animal for the production of a plurality of immortal B cells, producing a complete plurality of human antibodies against a human protein.

The invention further comprises a method for the generation and production of a monoclonal human antibody in a non-human animal, said antibody is directed against an human protein (including fragments) which is at least 80%, (BLAST) homologue to the corresponding protein of said non-human animal. Such an example is CXCR5. Human and murine CXCR5 are 84% homologous. The invention therefore provides a method to generate human antibodies against highly conservative proteins or protein regions, even if the protein or fragment thereof is at least 95% or more homologue between human and said non-human animal or even 100% homologue.

Therefore a further object of the invention is a monoclonal human antibody specific for a human protein having at least 95%, preferably 98% and even 100% homology (BLAST) to the corresponding protein of a non-human animal, preferably mouse, rat and/or rabbit. A preferred object of the invention is a monoclonal human antibody specific for a human protein having at least 95%, more preferably 98% and even 100% homology (BLAST) to the corresponding murine (mouse) protein.

The invention also comprises a method for the recombinant production of an antibody, characterized in contacting a new borne immune deficient non-human animal with a FL cell, subsequently contacting said non-human animal with a antigen, collecting from said non-human animal a human cell producing human antibody against said antigen, and isolating said antibody, sequencing the variable regions, constructing expression vector(s) encoding heavy and/or light chain at least CDRs, combined with a human constant chain, expressing said vector(s) in appropriate host cell(s) and isolating said antibody (immunoreactive protein) from said host cell(s) or fermentation supernatant.

The invention also comprises a method for the recombinant production of an antibody, characterized in contacting a new borne immune deficient non-human animal with a FL cell, subsequently contacting said non-human animal with a antigen, collecting from said non-human animal a human cell producing human antibody against said antigen, and isolating mRNA from said human cell producing human antibody, generating antibody specific cDNA (e.g. by use of Immunoglobulin specific primers), constructing expression vector(s) encoding heavy and/or light chain at least CDRs, combined with a human constant chain, expressing said vector(s) in appropriate host cell(s) and isolating said antibody (immunoreactive protein) from said host cell(s) or fermentation supernatant.

The invention also comprises a method for the selection of an immortal cell producing a human antibody showing specific binding to an antigen, said method being characterized in providing a plurality of human B cells from the spleen of a non human animal producing a complete plurality of human antibodies, fusing said cells or a subset thereof with an immoral myeloma cell or immortalizing said B cells or subset by EBV transformation, and selecting a hybridoma cell producing a human antibody showing specific binding to said antigen.

The invention also comprises a method for the selection of a immortal cell producing an antibody showing specific binding affinity of at least $10^{-6}$ mol/l to a antigen in an amount of at least 1.5 µg/ml, said method being characterized in providing a plurality of human B cells from the spleen of a non human animal producing a complete plurality of human antibodies, fusing said cells or a subset thereof with an immoral myeloma cell or immortalizing said B cells or subset by EBV transformation, and selecting a hybridoma cell producing an antibody showing specific binding affinity of at least $10^{-6}$ mol/l to a antigen.

Preferably the amount of isolated antibody is at least 1.5 µg/ml, and preferably the antibody shows a specific binding affinity of at least $10^{-9}$ mol/l to said antigen.

The examples, references, sequence listing and figures contained herein are provided to aid the understanding of the present invention, the true scope of which is set forth in the appended claims. It is understood that modifications can be made in the procedures set forth without departing from the spirit of the invention.

Isolating of the antibody from the antibody producing cell, ascites, and/or the supernatant can be performed according to the methods known in the state of the art like chromatography or dialysis. For example the antibody can be purified using one or more of a method selected from immunoaffinity purification, ammonium sulphate precipitation, protein A/G purification, ion exchange chromatography, gel filtration and/or ammonium sulphate precipitation. Such methods are described in Nau, D. R., Optimization of monoclonal antibody purification, In: Techniques in Protein Chemistry, Hugli, T. (ed.), Academic Press, New York, 1989, pp. 339-347; Coligan, J. E. et al. (eds.), Current Protocols in Immunology, John Wiley & Sons, Inc. (2005).

Instead of hybridoma generation alternative methods can be used for the production of an antibody according to the invention. Sud methods are e.g. based on the identification of the nucleic acid sequence of the antibody. Usually it is sufficient to identify the sequence of the variable regions, the CDR regions or even only the heavy chain CDR3 region. Preferably mRNA is isolated from a pool of antibody producing cells and is used to construct a cDNA-bank coding such region(s) in an appropriate expression vector. The cDNA-library is transfected into the host cells such as NS0 or CHO and screened for specific antibody production and specific clones are identified and isolated and used for the antibody production without hybridoma generation.

FL cells are stem cells that are capable of developing into various blood cell types e.g., B cells, T cells, granulocytes, platelets, and erythrocytes. Human hematopoietic fetal liver stem cells commonly express the surface antigen(s) CD31, CD34, CD117 (c-kit) and/or CD133. According to the invention there is used preferably a FL cell expressing CD133. As FL cell also a precursor cell (i.e. embryonic stem cell) can be used which develops after treatment with cytokines into a FL cell.

FL cells expressing CD133 can be isolated from human fetal liver and are further separated by CD 133 lineage, preferably by a immunomagnetic separation procedure e.g. Miltenyi "MACS® separation system". Another preferred method of isolating FL cells includes the additional steps of labeling the monocytes with a biotin-conjugated CD133 antibody and recovering a CD133 positive stem cell population.

Mice carrying a null mutation of cytokine receptor common gamma chain (γc) on the X chromosome have been described by DiSanto, J. P. et al, Proc. Natl. Acad. Sci. USA 92 (1995) 377-381. $γc^{-/-}$ females can be crossed with males homozygous for a mutation disrupting the RAG2 gene (Shinkai, Y. et al., Cell 68 (1992) 855-867). F1 males heterozygous for RAG2 deletion and hemizygous for γc deletion can be backcrossed onto $γc^{-/}$-$RAG2^{+/+}$ females. The RAG2 genotype of the resulting offspring can be determined by tail DNA PCR (Horton, R. M. et al., BioTechniques 19 (1995) 690-691). RAG2 heterozygotes are bred to produce the $γc^{-/-}$RAG2$^{-/-}$ female and $γc^{-/y}$RAG2$^{-/-}$ male mice ($γc^{-}$/RAG2$^{-}$). These mice have a mixed background of 129 Ola, Balb/c and C57BL/6.

Immunoreconstituton according to the invention occurs by transplantation of appropriate amounts of human FL cells into the liver of newborn and pre irradiated immunodeficient animals e.g. mice or rat.

The human monoclonal antibodies according to the invention can be produced by immunizing a immunoreconstituted non-human animal according to the invention, preferably a immunoreconstituted rodent, most preferably a immunoreconstituted rat or mouse, with a purified or enriched preparation of the antigen, nucleic acid encoding said antigen and/or cells expressing said antigen. B cells (e.g. splenic B cells) of the animal are then obtained and fused with an appropriate human fusion partner, like a myeloma cell to form immortal, hybridoma cells that secrete human monoclonal antibodies against the antigen via fusion with an appropriate human fusion partner, like a myeloma cell or by immortalization of said cells with e.g. EBV. For example, soluble antigens or fragments thereof are optionally conjugated to other molecules, and used as immunogens for generating antibodies. For transmembrane molecules, such as receptors, fragments of these (e.g. the extracellular domain of a receptor) can be used as the immunogen. Alternatively, cells expressing the transmembrane molecule can be used as the immunogen. Such cells can be derived from a natural source (e.g. cancer cell lines) or may be cells which have been transformed by recombinant techniques to express the transmembrane molecule. Other antigens and forms thereof useful for preparing antibodies will be apparent to those in the art.

Preferably, the immunoreconstituted non-human animal will be 6-16 weeks of age upon the first immunization. For example, a purified or enriched preparation of DNA encoding the antigen of interest (e.g. CD20 or HER3 antigen) can be used to immunize the immunereconstituted non-human animal according to the invention intramuscular. The immune response can be monitored over the course of the immunization protocol with plasma samples being obtained by retroorbital bleeds. The plasma can be screened by ELISA, and immunoreconstituted non-human with sufficient titers of antibodies against said antigen can be used for immortalization of corresponding B cells. Mice can be boosted intravenously with the antigen of interest before sacrifice and removal of the spleen and lymph nodes and peripheral blood.

It was found that 2-3 fusions for each antigen may need to be performed. Several mice will be immunized for each antigen.

The mouse lymphocytes can be isolated and fused with a human- or heteromyeloma cell using PEG or electrofusion based on standard protocols to generate hybridomas. Electrofusion is based upon a reversible structural change of the cell membranes, which is caused by the effects of an electrical field and is applicable for a wide spectrum of cells for fusion of two or more cells of the same or different origins, including their complete structures (nucleus, membranes, organelle, cell plasma) to create a new, viable cell.

The resulting hybridomas are then screened for the production of antigen-specific antibodies. For example, single cell suspensions of splenic and lymph node-derived lymphocytes from immunized mice are fused to K6H6/B5 nonsecreting heteromyeloma cells (ATCC, CRL 1823). Cells are plated at approximately $2 \times 10^5$ in flat bottom microtiter plate, followed by about two weeks incubation in selective medium.

Individual wells are then screened by ELISA for human monoclonal antibodies against the antigen (e.g. IgG). Once extensive hybridoma growth occurs, medium is analyzed, usually after 10-14 days. The antibody secreting hybridomas are replated, screened again, and if still positive for human monoclonal antibodies against the antigen, can be subcloned at least twice by limiting dilution. The stable subclones are then cultured in vitro to produce antibody in tissue culture medium for characterization.

The antigen may be introduced into the animal by any suitable means. Preferably, the animal is immunised intrasplenically, intravenously, intraperitoneally, intradermally intramuscular, subcutaneously alone or in combination with appropriate immunomodulate agents (e.g. CFA). Dose of each antigen should referably be in the range of between 1-500 μg.

Preferably, the method of the invention comprises the additional step of supplying the animal with a booster dose of the antigen 1-500 μg a booster 7-28 days after the last injection. Preferably, the animals are boosted 1 to 5 times.

Immunisation of the animal may be carried out with or without pharmaceutical carriers. Suitable carriers are e.g. IFA, Al3(OH)4, Abisco.

Additionally, these carriers may function as immunostimulating agents ("adjuvants"). Immunisation of the animal may be carried out with or without adjuvants in addition to the pharmaceutical carriers.

Preferred adjuvants to enhance effectiveness of the composition include, but are not limited to: e.g. CFA, IFA, Al3(OH)4, Abisco.

Preferred antibody-producing cells for use in the invention include B cells. These antibody-producing cells for use in the invention may be recovered by removal of any suitable cellular components of the immune system from the animal. Preferably, antibody-producing cells are recovered from the animal by removal of the spleen, lymph nodes, peripheral blood or bone marrow or portions thereof.

EXAMPLES

Materials & Methods

Mice: Rag2$^{-/-}$γc$^{-/-}$ mice on a BALB/c background were bred and maintained underspecific pathogen-free conditions in accordance with the guidelines of the ICH, AAALAC and EU Directive on Animal Welfare, 86/609.

Newborn repopulation assay: At day of birth, newborn mice were irradiated in a 3-4 hour interval with 2×2 Gy from a Cesium 137 source (Biobeam 8000, STS GmbH, Braunschweig, Germany) at 2 Gy/min., a dose that was titrated to be sub lethal. At 4-12 hours post irradiation, mice were transplanted with e.g. CD133+ FL cells alone or in combination with non hematopoietic CD133⁻ liver cells in 25 µl PBS or in combination with growth factors into the liver (i.h.) using a 30-gauge needle (Hamilton Bonaduz AG, Bonaduz, Switzerland). Newborns always received cells from single donors. Mice were weaned at 3 weeks of age. Analysis of mice: to obtain peripheral blood cells and plasma, mice were bled from retroorbital venous sinus under ether anesthesia.

Flow cytometric analysis and cell sorting. For FACS analysis and cell sorting monoclonal antibodies, biotinylated or conjugated with either FITC, PE, or APC against the following antigens were used: CD3 (UCHT1), CD4 (13B8.2), CD8 (B9.11), CD40 (MAB89), CD80 (MAB104), CD83 (HB15a), CD86 (HA5.2B7) (all Imunotech/Beckman Coulter, Marseille, France), CD19 (HIB19), CD20 (2H7), CD34(581), IL-3Ra/CD123 (9F5), CD11c (B-1y6) CD14 (M5E2) (all BD Pharmingen, San Diego, Calif.), CD45 (HI30), CD45RA (MEM56), HLA-DR (TU36) (all Caltag, Burlingame, Calif.), TLR2 (TL2.1), TLRR4 (HTA125), TCRab (IP26), (alleBioscience, San Diego, Calif.), BDCA-1, BDCA-2, BDCA-4, CD25 (4E3) (allMiltenyi Biotec), IgM (Jackson Immunoresearch, West Grove, Pa.), CCR7 (3D12, provided by M. Lipp, Berlin, Germany). The IOTest Beta Mark was used for Vbanalysis (Imunotech/Beckman Coulter). Streptavidin conjugated FITC, PE, or APC (all BD Pharmingen) were used for visualization of biotinylated antibodies. Dead cells were excluded by propidium iodide staining. Appropriate isotype-matched, irrelevant control mAbs were used to determine the level of background staining. Cells were analyzed using a FACS calibur and sorted using a FACSVantage SE (Becton Dickinson Immunocytometry Systems, Mountain View, Calif.).

Fetal Liver Cells. Fetal liver cells sources: Cambrex Corp. USA and StemCell Technologies Corp. USA.

Example 1

Immunization Procedure of Reconstituted Mice

Three Rag2⁻/⁻γc⁻/⁻ mice (3 females), were immunized with 100 µg plasmid DNA coding for human HER3 protein. In total up to six immunizations were given intramuscular (i.m.). When serum titers of anti-HER3 were found to be sufficient, mice were additionally boosted three times with 30 µg of purified HER3 proteine in 100 µl PBS intravenously (i.v.) 3, 2 and 1 days before fusion.

Example 2

Figure 1:
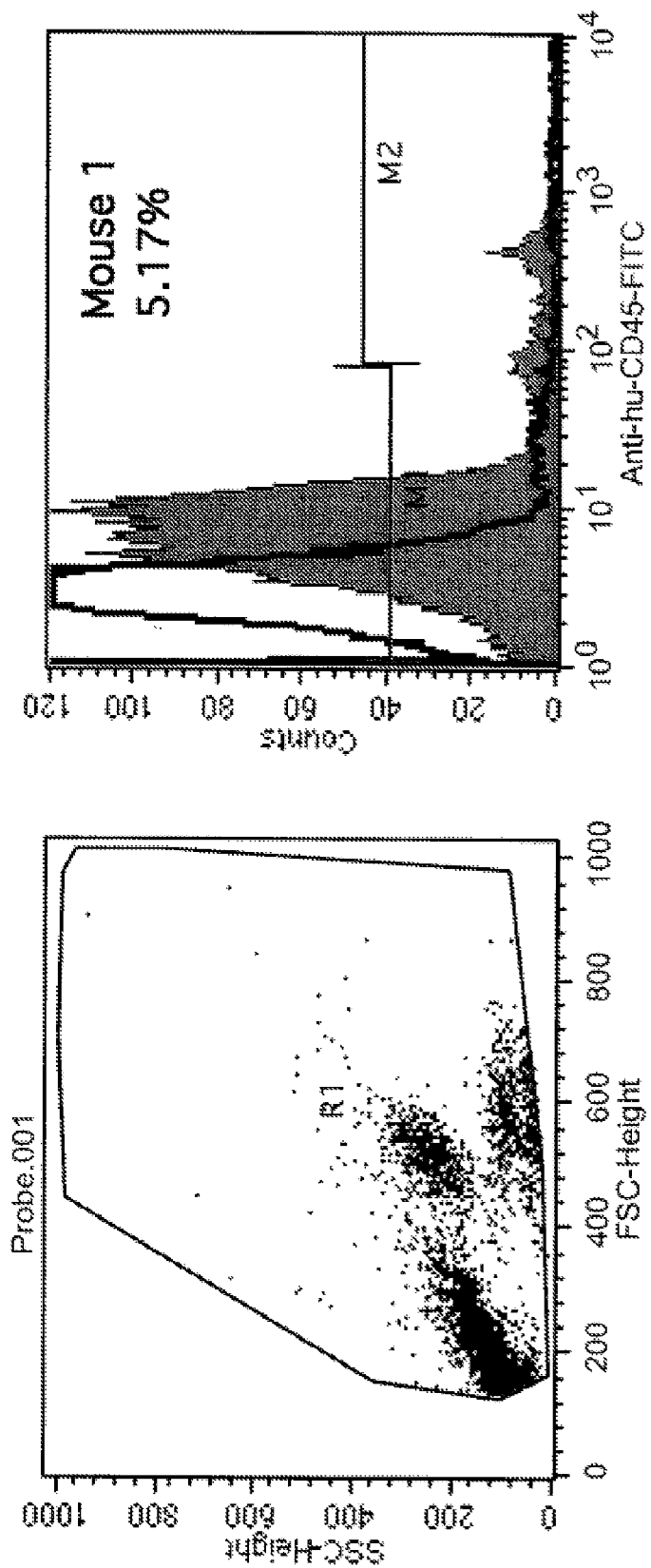
FIG. 1 Flowcytometric analysis of peripheral blood of reconstituted mice on 15th week after engraftment Human hematopoietic cell engraftment. Histograms shows overlay of viable gated peripheral blood cells from three representative animals at 15 weeks after reconstitution stained with anti human CD45-FITC mAb (filled area) or background staining from the same animal with isotyp-mached, irrelevant control mAb (dark line) which was used as denominator histogram for generating overlaid histogram statistics. Statistics represent number and percentage of events in designated sections (M1, M2) compared to total number of events within the gate. Shown are mean fluorescent intensities.
Figure 1B:
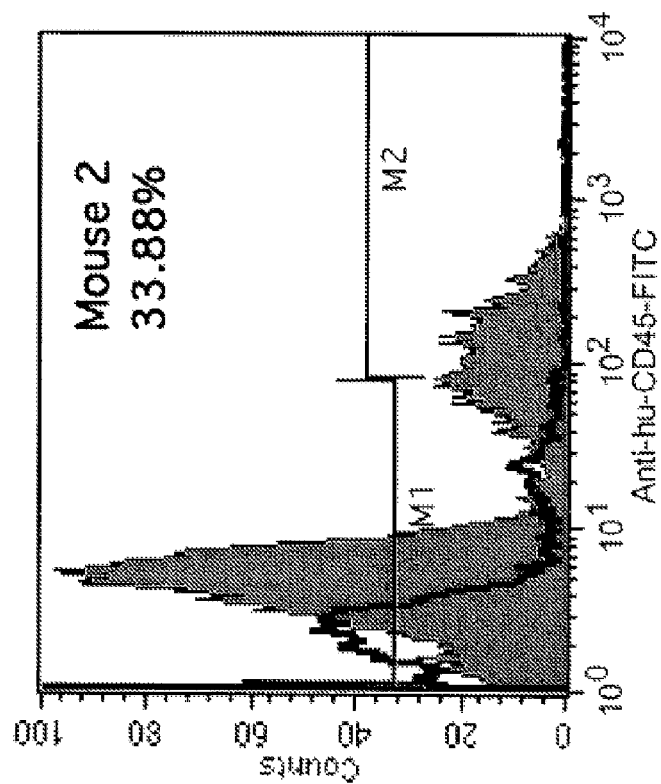
Figure 1B:
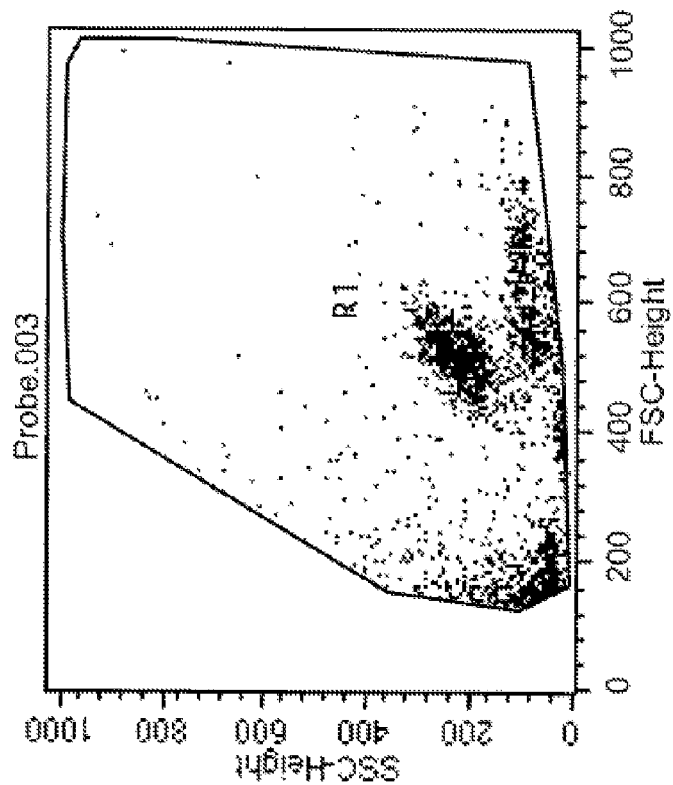
Figure 1C:
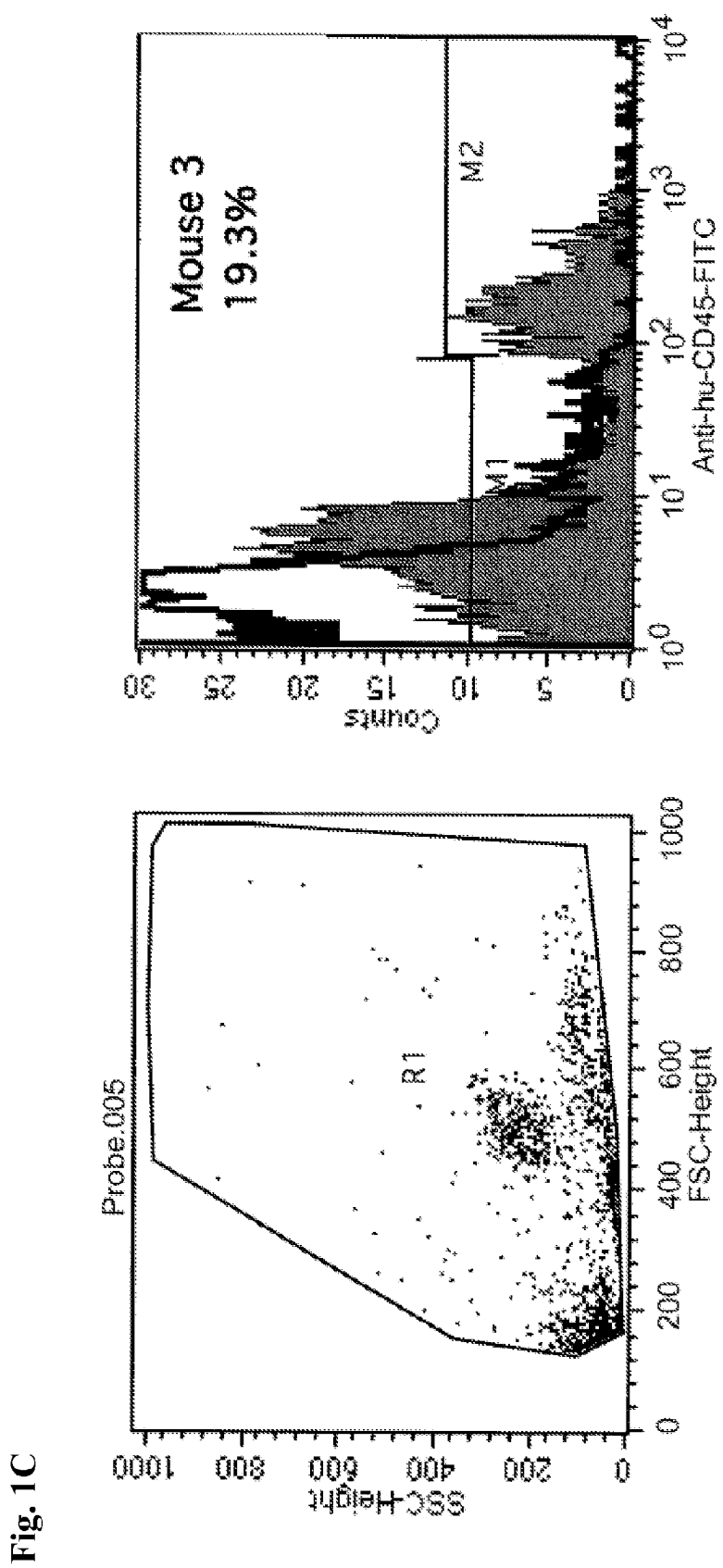

Flow Cytometric Analysis of Peripheral Blood of Reconstituted Mice on 15th Week After Engraftment The mice were isofluran-anaesthized and then peripheral blood was collected from the orbital vene plexus for measuring the positive ratio of human hemocytes by use of flow cytomenty. The collected blood was instantly blended well with EDTA-2Na and kept at room temperature until analysis. An optimum amount of FITC conjugated anti-human CD45 antibodies was added to and reacted with 50 µl of the whole blood at room temperature for 20 minutes. Thereafter, hemolysis and immobilization were effected using FACS solution and the ratio was measured using FACS Calibur. FIG. 1 shows ratio (%) of human CD45 positive cells in peripheral blood of three tested mice.

Example 3

Examination of the Production Ability of Human HER3 Antibodies in the Reconstituted Mice The amount of total human IgG in pheripheral blood of reconstituted mice was measured by ELISA. Diluted mice serum was coated on MaxiSorb 96 well plate (NUNC) and incubated for 1 h at room temperature. After blocking with 2% CroteinC solution for 1 h at room temperature washing was performed and thereafter peroxidase conjugated anti-human IgG monoclonal antibodies were added. After incubation for 45 minutes at room temperature washing was performed and ABTS substrate solution was added for 10 minute reaction at room temperature. Then the absorbance was measured at 405 nm (FIG. 2). The IgG concentration was calculated in accordance with the standard curve.

Example 4

Flow Cytometric Analysis of Human HER3 Antibodies in Peripheral Blood of Reconstituted Mice on 7th Week After Immunization 17 weeks after the reconstitution mice were immunized with human protein of interest. The immunization was performed intramuscular with 25-100 µg/mouse of DNA coding for an human protein of interest together with cytokine cocktail as adjuvant for enhancement of immunological response. The same immunization was performed every four weeks and serum was taken for measuring human protein specific antibodies by FACS. Briefly diluted anti serum was added to the human protein expressing cells and incubated for 20 minutes at room temperature. After washing an optimum amount of FITC conjugated anti-human antibodies were added to and reacted with cells for further 20 minutes at room temperature. Thereafter the positive ratio of stained human protein expressing cells was measured using FACS Calibur. FIG. 3 shows ratio (%) of human protein positive cells stained with different serum dilution (1/20 and 1/150) one of reconstituted and immunized mice compared to normal mouse serum (NMS) as negative control or to purified human protein specific antibodies as a positive control.

Example 5

Positive Selection of CD19⁺ Cells using Dynabeads®

CD19+ B cells were directly isolated from peripheral blood or splenocytes suspensions according the standard Dynal protocols Dynabeads® CD19 (Pan B) (product number111.03/111.04) and DETACHaBEAD® CD19 (Prod. No. 125.06):

Add 25 µl Dynabeads® to e.g. 2.5×10⁷ prepared cells
Incubate for 20 min at 2-8° C. with gentle tilting and rotation.
Place the tube in a magnet for 2 min
Discard the supernatant and gently wash the beadbound cells 4 times, using the following procedure:
Add 1 ml Buffer 1 per 1×10⁷ Dynabeads®.
Place the tube in the magnet for 1 min and discard the supernatant.
Resuspend the cells in buffer/medium for downstream application.

Example 6

Electrofusion for Hybridoma Generation

Isolated CD19+ cells were counted and fused via electrofusion protocols (Eppendorf applications for Electrofusion No. 58):

Harvest both isolated CD19+ cells and fusion partner e.g. K6H6/B5 by centrifugation (200×g, 10 min RT).

Resuspend pellets in growth medium and determine the cell number.

Set cell number of each fusion partner to e.g. 3×105 per fusion.

Pipette both partners together and centrifuge at 200×g for 10 minutes and RT.

Wash the pellet twice in electro fusion buffer, centri fuge as described above

Resuspend the pellet in 200 µl electrofusion buffer per fusion

Fill the fusion chamber and fuse immediately (see application protocol to the Fusionapparat, Eppendorf)

Following fusion, allow the chambers to stand for 10 min at RT.

Rinse the chamber with medium and transfer fused cells to cloning plates.

Add HAT selection medium after 24-hour incubation (5% $CO_2$, 37° C.).

After 7-21 days incubation count and analyse hybrids.

Grown human hybridomas (40 clones) were analyzed 14 days after fusion for total and human protein specific IgG in established ELISA and at least 6 clones were detected as positive.

| Hybridoma | HER3 ELISA CONC (µg/ml) | IgG ELISA CONC (µg/ml) | IgF ELISA CONC (µg/ml) |
| --- | --- | --- | --- |
| G2:1 | 0.006 | 0.015 | <0 |
| G3:1 | 0.165 | 0.017 | <0 |
| C4:1 | <−0.001 | 0.015 | <0 |
| E9:1 | 0.001 | 0.010 | <0 |
| G9:1 | 0.002 | 0.020 | <0 |
| C10:1 | 0.055 | 0.014 | <−0.001 |

Example 7

Immunization Procedure of Reconstituted mice

Three $Rag2^{-/-}\gamma c^{-/-}$ mice (4 females), were immunized with 100 µg plasmid DNA coding for human CXCR5 proteine. In total up to six immunizations were given intramuscular (i.m.).

Boosting of Mice

When serum titers of anti-CXCR5 were found to be sufficient, mice were additionally boosted three times with $5 \times 10^6$ of CXCR5 expresing cells in 100 µl PBS intravenously (i.v.) 3, 2 and 1 days before fusion.

Example 8

Examination of the Production Ability of Human CXCR5 Antibodies in the Reconstituted Mice The amount of total human IgG in pheripheral blood of reconstituted mice was measured by ELISA. Diluted mice serum was coated on MaxiSorb 96 well plate (NUNC) and incubated for 1 h at room temperature. After blocking with 2% CroteinC solution for 1 h at room temperature washing was performed and thereafter peroxidase conjugated anti-human IgG monoclonal antibodies were added. After incubation for 45 minutes at room temperature washing was performed and ABTS substrate solution was added for 10 minute reaction at room temperature. Then the absorbance was measured at 405 nm (FIG. 4). The IgG concentration was calculated in accordance with the standard curve (250 µg/ml total human IgG).

Example 9

Analysis of Human CXCR5 Antibodies in Reconstituted Mice after Third Immunization The amount of human CXCR5 specific IgG in serum of reconstituted mice was measured by CXCR5 specific ELISA (FIG. 5). Diluted mice serum was coated on MaxiSorb 96 well plate (NUNC) and incubated for 1 h at room temperature. After blocking with 2% CroteinC solution for 1 h at room temperature washing was performed and thereafter peroxidase conjugated anti-human IgG monoclonal antibodies were added. After incubation for 45 minutes at room temperature washing was performed and ABTS substrate solution was added for 10 minute reaction at room temperature. Then the absorbance was measured at 405 nm.

The invention claimed is:

1. A method for the production of a human antibody from an immunodeficient mouse or rat, comprising
   contacting a newborn immunodeficient mouse or rat with a human hematopoietic fetal liver stem cell to generate a reconstituted mouse or rat,
   subsequently contacting said reconstituted mouse or rat with an antigen,
   collecting from said reconstituted mouse or rat a human B cell that produces a human antibody against said antigen, and
   isolating said antibody from said human B cell.

2. The method of claim 1, wherein said reconstituted mouse or rat is a $Rag2^{-/-}$, $\gamma c^{-/-}$ Rag 2−/−, NOD, or SCID beige mouse.

3. The method of claim 1, comprising using a combination of a human hematopoietic fetal liver stem cell and a human non hematopoietic fetal liver stem cell to generate said reconstituted mouse or rat.

4. The method of claim 1, wherein the antigen that is contacted with the reconstituted mouse or rat is selected from the group consisting of an antigen, an antigen fragment, a MHC/peptide complex, an antigen encoding DNA, and an antigen bearing cell.

5. The method of claim 1, further comprising fusing said human B cell with a human or heteromyeloma fusion partner cell line, wherein the fusion partner cell line is a MFP-2, HK-128, K6H6/B5 or Karpas 707 cell line.

6. A method for the production of a plurality of human B cells that produce a plurality of human antibodies against an antigen: comprising:
   a) contacting a newborn immune deficient rat or mouse with a human fetal liver stem cell to generate an immune reconstituted rat or mouse,
   b) subsequently contacting said immune reconstituted rat or mouse with an antigen, and
   c) collecting a plurality of human B cells that produce a plurality of human antibodies from said immune reconstituted rat or mouse.

7. A method for the recombinant production of a human antibody, comprising:
   (a) contacting a newborn immune deficient mouse or rat with a human fetal liver stem cell,
   (b) subsequent to step (a) contacting said mouse or rat with an antigen,
   (c) subsequent to step (b) collecting from said mouse or rat a human B cell that produces a human antibody against said antigen, and
   (d) isolating mRNA from said human B cell that encodes for the human antibody,
   (e) generating cDNA that encodes for the human antibody,
   (f) constructing expression vector(s) encoding heavy and/or light chain or at least complementary determining regions, alone or combined with DNA encoding a human constant chain,
   (g) expressing said vector(s) in appropriate host cell(s) to produce an antibody and
   (h) isolating said antibody from said host cell(s) or fermentation supernatant of said host cell(s).

8. A method for the selection of an immortal cell that produces a human antibody with specific binding to an antigen, comprising:
   using the method according to claim 1 to provide a plurality of human B cells isolated from the spleen of the reconstituted mouse or rat, wherein the human B cells produce a complete plurality of human antibodies,
   fusing said B cells, or a subset thereof, with an immortal myeloma cell, or immortalizing said B cells or a subset thereof by EBV transformation to produce a hybridoma cell, and
   selecting a hybridoma cell that produces a human antibody with specific binding to said antigen.

9. A method for the selection of an immortal cell that produces an antibody with specific binding affinity of at least $10^{-6}$ mol/L to an antigen, comprising:
   using the method according to claim 1 to provide a plurality of human B cells isolated from the spleen of the reconstituted mouse or rat, wherein the human B cells produce a complete plurality of human antibodies,
   fusing said B cells, or a subset thereof, with an immortal myeloma cell, or immortalizing said B cells or a subset thereof by EBV transformation to produce a hybridoma cell, and
   selecting a hybridoma cell producing an antibody with an affinity of at least $10^{-6}$ mol/L to said antigen.

10. The method of claim 1, wherein the human hematopoietic fetal liver stem cell is a CD133+ hematopoietic stem cell.

11. The method of claim 7, wherein the cDNA that encodes for the human antibody is generated by use of immunoglobulin specific primers.

* * * * *